US011925638B2

(12) United States Patent
Eguchi et al.

(10) Patent No.: US 11,925,638 B2
(45) Date of Patent: *Mar. 12, 2024

(54) PHARMACEUTICAL COMPOSITION COMPRISING DIAMINO HETEROCYCLIC CARBOXAMIDE COMPOUND AS ACTIVE INGREDIENT

(71) Applicant: ASTELLAS PHARMA INC., Tokyo (JP)

(72) Inventors: Tomohiro Eguchi, Tokyo (JP); Masamichi Mori, Tokyo (JP); Yoko Yamaki, Tokyo (JP)

(73) Assignee: ASTELLAS PHARMA INC., Tokyo (JP)

( * ) Notice: Subject to any disclaimer, the term of this patent is extended or adjusted under 35 U.S.C. 154(b) by 281 days.

This patent is subject to a terminal disclaimer.

(21) Appl. No.: 17/327,337

(22) Filed: May 21, 2021

(65) Prior Publication Data

US 2021/0290618 A1 Sep. 23, 2021

Related U.S. Application Data

(63) Continuation of application No. 15/116,736, filed as application No. PCT/JP2015/053018 on Feb. 3, 2015, now Pat. No. 11,045,468.

(30) Foreign Application Priority Data

Feb. 4, 2014 (JP) .................................. 2014-019226

(51) Int. Cl.
| | | |
|---|---|---|
| *A61K 31/497* | (2006.01) | |
| *A61K 31/517* | (2006.01) | |
| *A61K 31/5377* | (2006.01) | |
| *A61K 45/06* | (2006.01) | |

(52) U.S. Cl.
CPC .......... *A61K 31/497* (2013.01); *A61K 31/517* (2013.01); *A61K 31/5377* (2013.01); *A61K 45/06* (2013.01)

(58) Field of Classification Search
CPC .................................................. A61K 31/497
See application file for complete search history.

(56) References Cited

U.S. PATENT DOCUMENTS

| | | | |
|---|---|---|---|
| 8,969,336 B2 | 3/2015 | Shimada | |
| 10,786,500 B2* | 9/2020 | Miyazaki | A61P 35/00 |
| 11,045,468 B2* | 6/2021 | Eguchi | A61P 35/02 |
| 2011/0110923 A1 | 5/2011 | Lee | |
| 2012/0040968 A1 | 2/2012 | Shimada et al. | |
| 2013/0053376 A1 | 2/2013 | Gregor et al. | |
| 2013/0150363 A1 | 6/2013 | Gilmer et al. | |
| 2013/0156796 A1 | 6/2013 | Setiady | |
| 2014/0141000 A1 | 5/2014 | Chiu | |
| 2014/0221425 A1 | 8/2014 | Yun et al. | |
| 2014/0371196 A1 | 12/2014 | Shimada et al. | |

FOREIGN PATENT DOCUMENTS

| | | |
|---|---|---|
| BR | PI 1011838-1 A2 | 2/2018 |
| CN | 102421761 A | 4/2012 |
| EP | 2 428 508 | 3/2012 |
| JP | 2011/515397 A | 5/2011 |
| WO | 2010/128659 A1 | 11/2010 |
| WO | 2013/040801 A1 | 3/2013 |
| WO | WO 2015/127234 | 8/2015 |

OTHER PUBLICATIONS

Chinese Office Action issued Nov. 23, 2022 in Chinese Patent Application No. 201580006772.9 (with English translation), 14 pages.
Liao et al., "Lung Cancer", Shanghai Science and Technology Press, 2012, pp. 495-496 (7 total pages) (with partial English translation).
Alexis Mollard, et al., "Design, Synthesis, and Biological Evaluation of a Series of Novel AXL Kinase Inhibitors," ACS Medicinal Chemistry Letters, 2011 American Chemical Society, vol. 2, No. 12, pp. 907-912.
F. Michael Yakes, et al., "Cabozantinib (XL184), a Novel MET and VEGFR2 Inhibitor: Simultaneously Suppresses Metastasis, Angiogenesis, and Tumor Growth," Molecular Cancer Therapeutics, vol. 10, No. 12, Dec. 2011, pp. 2298-2308.
Lauren Averett Byers, et al., "An Epithelial-Mesenchymal Transition Gene Signature Predicts Resistance to EGFR and PI3K Inhibitors and Identifies Axl as a Therapeutic Target for Overcoming EGFR Inhibitor Resistance," Clinical Cancer Research, vol. 19, No. 1, pp. 279-290, 2013.
International Search Report dated Mar. 31, 2015 in PCT/JP2015/053018 filed Feb. 3, 2015.
Office Action dated Mar. 27, 2019 in corresponding Israeli Patent Application No. 247077 (with English Translation), 6 pages.
Office Action dated Jul. 30, 2020 in the corresponding VN Patent Application No. 1-2016-02842 (with English Translation).
Office Action dated Sep. 13, 2018 in the corresponding Eurasian Patent Application No. 201691570/28 (wtc:ng11sn Translation).
Office Action dated Jul. 1, 2019 in the corresponding Ukrainian Patent Application No. a 2016 09187 (with English Translation).

(Continued)

*Primary Examiner* — Rei Tsang Shiao

(74) *Attorney, Agent, or Firm* — Oblon, McClelland, Maier & Neustadt, L.L.P.

(57) ABSTRACT

A pharmaceutical composition is suitable for treating AXL-related cancer. The cancer can be cancer with high expression of AXL. The cancer can also be cancer which has acquired resistance by the activation of AXL against therapy with an anticancer agent. Specific diamino heterocyclic carboxamide compounds have an AXL inhibitory action, and pharmaceutical compositions comprising these compounds as an active ingredient have a therapeutic effect on AXL-related cancer. This AXL-related cancer can be cancer with high expression of AXL and/or cancer which has acquired resistance by the activation of AXL against therapy with an anticancer agent.

7 Claims, 2 Drawing Sheets

(56) References Cited

OTHER PUBLICATIONS

Office Action dated Oct. 31, 2019 in the corresponding Saudi Arabian Patent Application No. 516371604 (with English Translation).
Office Action dated Nov. 13, 2019 in the corresponding Chinese Patent Application No. 201580006772.9 (with English Translation).
Office Action dated Jul. 29, 2019 in the corresponding Indonesian Patent Application No. P00201605104 (w/English Translation).
Office Action dated Apr. 5, 2019 in Saudi Arabia Patent Application No. 516371604 and English translation.
Office Action dated Mar. 12, 2019 in Philippine Patent Application No. 1-2016-501527.
Office Action dated Mar. 29, 2019 in Indian Patent Application No. 20167026442.
Office Action dated Oct. 11, 2018 in the corresponding Uzbekistan Patent Application No. IAP2016 0342 (w/English Translation).
Office Action dated Jul. 16, 2018 in the corresponding Colombian Patent Application No. C2016/0000649 with English Translation.
Office Action dated Aug. 27, 2018 in the corresponding Taiwanese Patent Application No. 104103756 (w/ English Translation).
Office Action dated Sep. 27, 2018 in the corresponding Mexican Patent Application No. MX/a/2016/10134 (w/English Translation).
Office Action dated May 24, 2018 in Chinese Patent Application No. 201580006772.9 (with English translation).
Office Action dated Jun. 6, 2018 in Philippine Patent Application Type/No. Invention 1/2016/501527.
Office Action dated Feb. 7, 2018 in Eurasian Patent Application No. 201691570128 (with English translation).
X. Wu, et al., Oncotarget, vol. 5, No. 20, pp. 9546-9563 (2014).
Office Action dated Jul. 6, 2017 in Eurasian Patent Application No. 201691570 (with English language translation).
Supplementary European Search Report dated Aug. 16, 2017 in Patent Application No. 15746276.3.
Extended European Search Report dated Jul. 4, 2017 in Patent Application No. 15746276.3.
Rafael Rosell, et al. "Genetics and biomarkers in personalisation of lung cancer treatment," Lancet, XP055098533, vol. 382, No. 9893, 2013, pp. 720-731.
Office Action dated Feb. 3, 2017 in Colombian Patent Application No. NC2016/0000649 (English translation only).
Office Action dated May 23, 2017 in Singapore Patent Application No. 11201606413R.
English translation of the Written Opinion dated Mar. 31, 2015 in PCT/JP2015/053018.
Algerian Office Action dated Jan. 26, 2017 in Patent Application No. DZ/P/2016/000403 (with English Translation).
Postel-Vinay et al., "AXL and acquired resistance to EGFR inhibitors", Nature Genetics, 2012, vol. 44, No. 8, pp. 835-836 (Year: 2012).
Zhang et al., "Activation of the AXL kinase causes resistance to EGFR-targeted therapy in lung cancer", Nature Genetics, 2012, vol. 44, No. 8, pp. 852-860 (Year: 2012).
Aaron S. Meyer et al., "The Receptor AXL Diversifies EGFR Signaling and Limits the Response to EGFR-Targeted Inhibitors in Triple-Negative Breast Cancer Cells", Science Signaling 6; No. 287 (Aug. 6, 2013): ra66-ra66, 15 pages (http://dx.doi.org/10.1126/scisignal.2004155).
Combined Chinese Office Action and Search Report dated Jun. 1, 2023, in corresponding Chinese Patent Application No. 2021108801883 (with English Translation), 18 pages.
Meilin Liao et al., "Lung cancer, 3rd edition", Shanghai Scientific and Technical Publishers, pp. 482-484, published on May 31, 2012.
Yufei Feng et al., "Handbook of FDA Approved New Drugs, 1st edition", People's Military Medical Publisher, pp. 104-105, published on Jan. 31, 2011.

* cited by examiner

PHARMACEUTICAL COMPOSITION COMPRISING DIAMINO HETEROCYCLIC CARBOXAMIDE COMPOUND AS ACTIVE INGREDIENT

The present application is continuation of U.S. application Ser. No. 15/116,736, filed Aug. 4, 2016, which is a National Stage entry under 35 USC 371 of PCT/JP2015/053018, filed on Feb. 3, 2015, which claims priority to Japanese Patent Application No. 2014-019226 filed on Feb. 4, 2014. The contents of these applications are incorporated herein by reference in their entirety.

TECHNICAL FIELD

The present invention relates to a pharmaceutical composition for treating AXL-related cancer comprising, for example, a diamino heterocyclic carboxamide compound or a pharmaceutically acceptable salt thereof as an active ingredient.

BACKGROUND ART

AXL is a receptor-type tyrosine kinase, which is a protein having a cellular transmembrane domain at the center, a tyrosine kinase domain at the carboxyl terminus, and an extracellular region at the amino terminus. Overexpression of AXL in acute leukemia, astrocytoma, breast cancer, colon cancer, esophageal cancer, gastrointestinal stromal tumor, gastric cancer, hepatocellular cancer, Kaposi's sarcoma, lung cancer, melanoma, ovarian cancer, bone sarcoma, pancreatic ductal adenocarcinoma, renal cell cancer, prostate cancer, thyroid cancer, and endometrial cancer has hitherto been reported (Mol. Cancer Ther. 2011 October; 10(10): 1763-73).

Further, resistance acquisition by the activation of AXL against therapy with an anticancer agent has recently been reported. For example, in non-small cell lung cancer (NSCLC) with activating mutations of EGFR, there are many cases where inhibition of tumor growth is induced by an EGFR tyrosine kinase inhibitor (hereinafter referred to as an "EGFR inhibitor" in some cases) such as erlotinib and gefitinib, but this effect is not sustained and the tumor acquires resistance and starts reproliferation. As a result of the analysis of a sample of NSCLC which has acquired resistance to erlotinib, increased expression of AXL and, in some cases, increased expression of GAS6 which is a ligand of AXL were observed (Nat. Genet. 2012 Jul. 1; 44(8): 852-60). Similar results are shown in non-clinical trials. EGFR mutation-positive HCC827 lung cancer cell lines are erlotinib-sensitive, but when erlotinib-resistant HCC827 cells were obtained through in-vitro erlotinib exposure, overexpression of AXL was exhibited. When AXL was suppressed in molecular biology techniques in this cell, sensitivity to erlotinib was restored. In contrast, HCC827 with stably expressing AXL, to which AXL genes had been introduced, exhibited erlotinib resistance (Nat. Genet. 2012 Jul. 1; 44(8): 852-60).

In addition to lung cancer cells, increased expression of AXL is also observed in head-and-neck cancer cell lines which have acquired resistance to erlotinib, and it is reported that sensitivity to erlotinib is exhibited by an AXL inhibitor or by suppressing AXL in molecular biology techniques (Mol. Cancer Ther. 2013 November; 12(11): 2541-58).

It is reported that in estrogen hormone receptor-, progesterone hormone receptor-, and an HER2 receptor-negative breast cancer cells, the cells with high expression of AXL also exhibit resistance to an EGFR inhibitor (Sci. Signal. 2013 Aug. 6; 6(287): ra66).

AXL and resistance to chemotherapy have been reported with regard to various cancers. From the viewpoint that cells which has acquired resistance to chemotherapy exhibit overexpression of AXL in a clinical sample with acute myeloid leukemia (AML) and AML cell lines stably expressing AXL also exhibit resistance to chemotherapy, AXL is considered to be a cause of resistance to therapy (Cancer Lett. 2008 Sep. 18; 268(2): 314-24). Also in clinical sample with astrocytoma, overexpression of AXL is seen, which is a poor prognosis factor. Further, in astrocytoma cell lines that exhibits high expression of AXL, enhancement in sensitivity to temozolomide or carboplatin which is the first-line therapy is seen by inhibiting AXL with siRNA (Mol. Cancer Ther. 2010 May; 9(5): 1298-307). Also in a clinical sample with esophageal cancer, high expression of AXL is observed, and in esophageal cancer cell lines, the sensitivity to cisplatin is increased by inhibiting AXL with siRNA, whereas the resistance to cisplatin is acquired by the overexpression of AXL (Cancer Res. 2013 Jan. 1; 73(1): 331-40). In lung cancer cells which is not EGFR mutation-positive, cisplatin is the first-line drug and extension of the overall survival period is observed, but after continuously administering cisplatin, appearance of resistant cancer is observed. When cisplatin-resistant cancer in lung cancer cell lines is established, high expression of AXL is observed, and sensitivity to cisplatin is increased by inhibiting AXL with siRNA (Cancer Sci. 2013 July; 104(7): 904-11).

It is known that 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide (hereinafter referred to as a "compound A" in some cases) or a pharmaceutically acceptable salt thereof is useful as an active ingredient of a pharmaceutical composition for treating cancer (Patent Document 1).

In Patent Document 1, the compound A or a pharmaceutically acceptable salt thereof is disclosed as a free form and as a hemifumarate salt in Examples 547 and 577, respectively, and their inhibitory actions against various kinases, that is, ALK (Test Examples 1 to 4), RET (Test Example 5), ROS (Test Example 6), and FLT3 (Test Example 7), are confirmed. In addition, this document teaches that some compounds described in the document exhibit a 50% or higher inhibitory action against seven kinds of kinases at 5 nM concentration among various 78 kinds of kinases (Test Example 8). However, although AXL is included in the various 78 kinds of kinases, there is neither description nor suggestion that the compound exhibits an inhibitory action against AXL, and there is no description which compound described in this document the compound corresponds to.

RELATED ART

Patent Document

[Patent Document 1] WO 2010/128659

DISCLOSURE OF INVENTION

Technical Problem

Problems to be Solved by the Invention

There is provided a pharmaceutical composition for treating AXL-related cancer, in one aspect, a pharmaceutical composition for treating cancer with high expression of AXL, and in another aspect, a pharmaceutical composition for treating cancer which has acquired resistance by the activation of AXL against therapy with an anticancer agent Means for Solving the Problems The present inventors have conducted extensive studies for the purpose of creating a pharmaceutical composition for treating cancer, and as a result, they have found that 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof has an excellent AXL inhibitory action, and a pharmaceutical composition comprising this compound or a pharmaceutically acceptable salt thereof as an active ingredient is useful as a pharmaceutical composition for treating AXL-related cancer, in one aspect, a pharmaceutical composition for treating cancer with high expression of AXL, and in another aspect, a pharmaceutical composition for treating cancer which has acquired resistance by the activation of AXL against therapy with an anticancer agent, thereby completing the present invention.

That is, the present invention relates to a pharmaceutical composition for treating AXL-related cancer, in one aspect, a pharmaceutical composition for treating cancer with high expression of AXL, and in another aspect, a pharmaceutical composition for treating cancer which has acquired resistance by the activation of AXL against therapy with an anticancer agent, comprising 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof, and a pharmaceutically acceptable excipient.

Moreover, the present invention relates to an agent for treating AXL-related cancer, in one aspect, an agent for treating cancer with high expression of AXL, and in another aspect, an agent for treating cancer which has acquired resistance by the activation of AXL against therapy with an anticancer agent, comprising a compound A or a pharmaceutically acceptable salt thereof.

The present invention further relates to use of the compound A or a pharmaceutically acceptable salt thereof for the manufacture of a pharmaceutical composition for treating AXL-related cancer, in one aspect, for the manufacture of a pharmaceutical composition for treating cancer with high expression of AXL, and in another aspect, for the manufacture of a pharmaceutical composition for treating cancer which has acquired resistance by the activation of AXL against therapy with an anticancer agent; use of the compound A or a pharmaceutically acceptable salt thereof for treating AXL-related cancer, in one aspect, for treating cancer with high expression of AXL, and in another aspect, for treating cancer which has acquired resistance by the activation of AXL against therapy with an anticancer agent; the compound A or a pharmaceutically acceptable salt thereof for treating AXL-related cancer, in one aspect, for treating cancer with high expression of AXL, in another aspect, for treating cancer which has acquired resistance by the activation of AXL against therapy with an anticancer agent; and a method for treating AXL-related cancer, comprising administering an effective amount of the compound A or a pharmaceutically acceptable salt thereof to a subject, in one aspect, a method for treating cancer with high expression of AXL, comprising administering an effective amount of the compound A or a pharmaceutically acceptable salt thereof to a subject, and in another aspect, a method for treating cancer which has acquired resistance by the activation of AXL against therapy with an anticancer agent, comprising administering an effective amount of the compound A or a pharmaceutically acceptable salt thereof to a subject. In addition, the "subject" is a human or non-human animal in need of treatment thereof, and in one aspect, a human in need of treatment thereof.

Effects of the Invention

The compound A or a pharmaceutically acceptable salt thereof which is an active ingredient of the pharmaceutical composition of the present invention has an AXL inhibitory action, and can be used as an active ingredient of a pharmaceutical composition for treating AXL-related cancer, in one aspect, a pharmaceutical composition for treating cancer with high expression of AXL, and in another aspect, a pharmaceutical composition for treating cancer which has acquired resistance by the activation of AXL against therapy with an anticancer agent.

EMBODIMENTS FOR CARRYING OUT THE INVENTION

Figure 1:
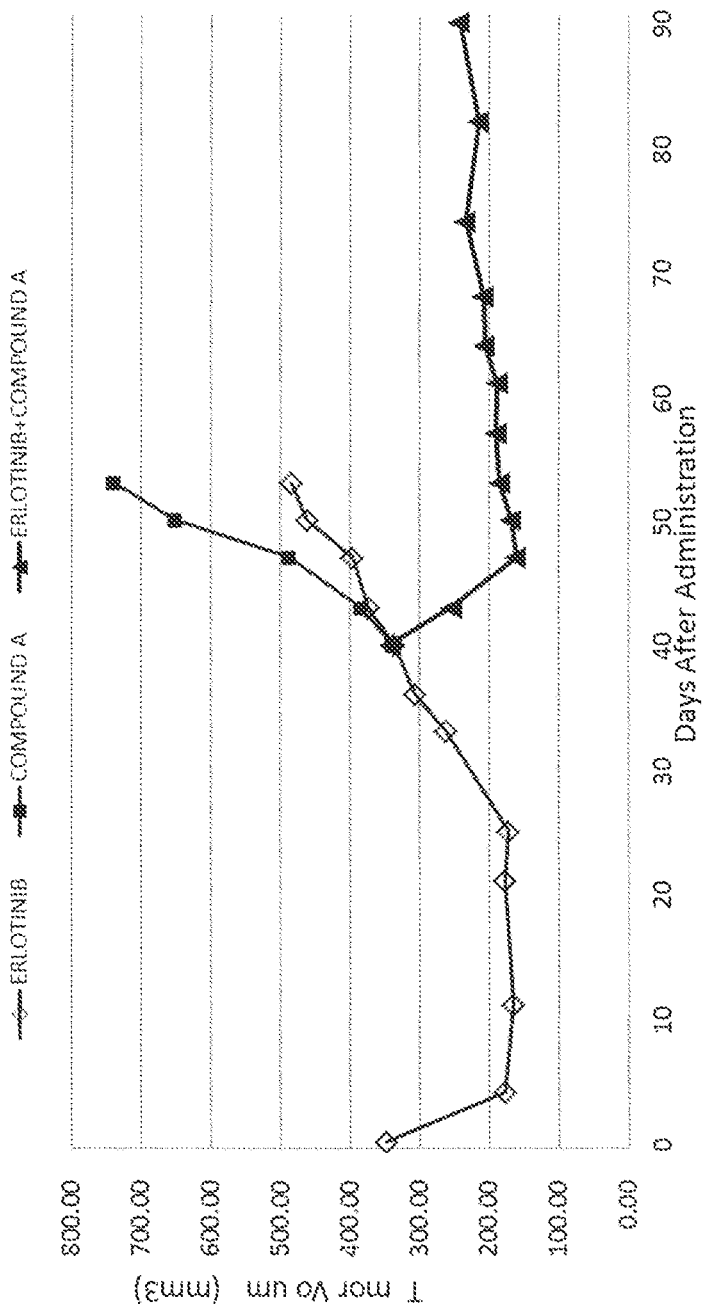
FIG. 1 is a view showing a process in preparing an erlotinib-resistant HCC827 subcutaneous cancer-bearing model mouse by administering erlotinib to an HCC827 subcutaneous cancer-bearing mouse; and then the tumor volumes of the model animals in the erlotinib-administered group, the compound A-administered group, and the group with combined use of erlotinib and the compound A. The vertical axis indicates the tumor volumes and the horizontal axis indicates the number of days.

Hereinbelow, the present invention will be described in detail.

As described above, the chemical name of the compound A is 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide and its chemical structure is as shown below.

[Chem. 1]

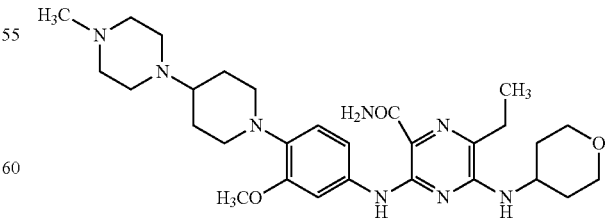

The AXL-related cancer means cancer in which one of the causes of the cancer is AXL, and examples thereof include cancer with high expression of AXL, and cancer which has acquired resistance by the activation of AXL against therapy with an anticancer agent. Examples of the cancer with high expression of AXL include cancers of acute leukemia, astrocytoma, breast cancer, colon cancer, esophageal cancer, gastrointestinal stromal tumor, gastric cancer, hepatocellular cancer, Kaposi's sarcoma, lung cancer, melanoma, ovarian cancer, bone sarcoma, pancreatic ductal adenocarcinoma, renal cell cancer, prostate cancer, thyroid cancer, and endometrial cancer, in each of which AXL is overexpressed, as compared with normal tissues. Incidentally, examples of the cancer which has acquired resistance by the activation of AXL against therapy with an anticancer agent include non-small cell lung cancer, head-and-neck cancer, and estrogen hormone receptor-, progesterone hormone receptor-, and HER2 receptor-negative breast cancer (triple negative breast cancer), each of which has activating mutations of EGFR, which has acquired resistance to therapy with an EGFR inhibitor; acute myeloid leukemia and astrocytoma, each of which has acquired resistance to chemotherapy; and lung cancer which is not EGFR mutation-positive and has acquired resistance to therapy with cisplatin.

Examples of the EGFR inhibitor that is used for non-small cell lung cancer, head-and-neck cancer and triple negative breast cancer, each having activating mutations of EGFR which has acquired resistance to therapy with an EGFR inhibitor, include erlotinib, gefitinib, and lapatinib, in one aspect, erlotinib and gefitinib, and in another aspect, erlotinib. Examples of the chemotherapeutic agent that is used for acute myeloid leukemia and astrocytoma, each of which has acquired resistance to chemotherapy, include cytarabine, enocitabine, idarubicin, daunorubicin, or a combination thereof.

In the case where a pharmaceutical composition comprising the compound A or a pharmaceutically acceptable salt thereof of the present invention is used to treat cancer which has acquired resistance by the activation of AXL against therapy with an anticancer agent, it is preferably used in combination with the anticancer agent.

Some aspects of the present invention will be shown below.

(1-1) A pharmaceutical composition for treating AXL-related cancer, comprising the compound A and a pharmaceutically acceptable excipient, in one aspect, a pharmaceutical composition for treating cancer with high expression of AXL, comprising a compound A and a pharmaceutically acceptable excipient, and in another aspect, a pharmaceutical composition for treating cancer which has acquired resistance by the activation of AXL against therapy with an anticancer agent, comprising a compound A and a pharmaceutically acceptable excipient.

(1-2) Use of the compound A for the manufacture of a pharmaceutical composition for treating AXL-related cancer, in one aspect, use of the compound A for the manufacture of a pharmaceutical composition for treating cancer with high expression of AXL, and in another aspect, use of the compound A for the manufacture of a pharmaceutical composition for treating cancer which has acquired resistance by the activation of AXL against therapy with an anticancer agent.

(1-3) Use of the compound A for treating AXL-related cancer, in one aspect, use of the compound A for treating cancer with high expression of AXL, and in another aspect, use of the compound A for treating cancer which has acquired resistance by the activation of AXL against therapy with an anticancer agent.

(1-4) The compound A for treating AXL-related cancer, in one aspect, the compound A for treating cancer with high expression of AXL, and in another aspect, the compound A for treating cancer which has acquired resistance by the activation of AXL against therapy with an anticancer agent.

(1-5) A method for treating AXL-related cancer, comprising administering an effective amount of the compound A to a subject, in one aspect, a method for treating cancer with high expression of AXL, comprising administering an effective amount of the compound A to a subject, and in another aspect, a method for treating cancer which has acquired resistance by the activation of AXL against therapy with an anticancer agent, comprising administering an effective amount of the compound A to a subject.

(2-1) A pharmaceutical composition for treating AXL-related cancer, comprising hemifumarate of the compound A, and a pharmaceutically acceptable excipient, in one aspect, a pharmaceutical composition for treating cancer with high expression of AXL, comprising hemifumarate of the compound A, and a pharmaceutically acceptable excipient, and in another aspect, a pharmaceutical composition for treating cancer which has acquired resistance by the activation of AXL against therapy with an anticancer agent, comprising hemifumarate of the compound A, and a pharmaceutically acceptable excipient.

(2-2) Use of hemifumarate of the compound A for the manufacture of a pharmaceutical composition for treating AXL-related cancer, in one aspect, use of hemifumarate of the compound A for the manufacture of a pharmaceutical composition for treating cancer with high expression of AXL, and in another aspect, use of hemifumarate of the compound A for the manufacture of a pharmaceutical composition for treating cancer which has acquired resistance by the activation of AXL against therapy with an anticancer agent.

(2-3) Use of hemifumarate of the compound A for treating AXL-related cancer, in one aspect, use of hemifumarate of the compound A for treating cancer with high expression of AXL, and in another aspect, use of hemifumarate of the compound A for treating cancer which has acquired resistance by the activation of AXL against therapy with an anticancer agent.

(2-4) Hemifumarate of the compound A for treating AXL-related cancer, in one aspect, hemifumarate of the compound A for treating cancer with high expression of AXL, and in another aspect, hemifumarate of the compound A for treating cancer which has acquired resistance by the activation of AXL against therapy with an anticancer agent.

(2-5) A method for treating AXL-related cancer, comprising administering an effective amount of hemifumarate of the compound A to a subject, in one aspect, a method for treating cancer with high expression of AXL, comprising administering an effective amount of hemifumarate of the compound A to a subject, and in another aspect, a method for treating cancer which has acquired resistance by the activation of AXL against therapy with an anticancer agent, comprising administering an effective amount of hemifumarate of the compound A to a subject.

(3) The pharmaceutical composition as described in (1-1) or (2-1); the use as described in (1-2) or (2-2); the use as described in (1-3) or (2-3); the compound A as described in (1-4) or hemifumarate of the compound A as described in (2-4); or the treating method as described in (1-5) or (2-5), in which the AXL-related cancer is cancer with high expression of AXL or cancer which has acquired resistance by the activation of AXL against therapy with an anticancer agent.

(4) The pharmaceutical composition as described in (1-1) or (2-1); the use as described in (1-2) or (2-2); the use as described in (1-3) or (2-3); the compound A as described in (1-4) or hemifumarate of the compound A as described in (2-4); or the treating method as described in (1-5) or (2-5), in which the cancer with high expression of AXL is acute leukemia, astrocytoma, breast cancer, colon cancer, esophageal cancer, gastrointestinal stromal tumor, gastric cancer, hepatocellular cancer, Kaposi's sarcoma, lung cancer, melanoma, ovarian cancer, bone sarcoma, pancreatic ductal adenocarcinoma, renal cell cancer, prostate cancer, thyroid cancer, or endometrial cancer, in each of which AXL is overexpressed.

(5) The pharmaceutical composition as described in (1-1) or (2-1); the use as described in (1-2) or (2-2); the use as described in (1-3) or (2-3); the compound A as described in (1-4) or hemifumarate of the compound A as described in (2-4); or the treating method as described in (1-5) or (2-5), in which the cancer which has acquired resistance by the activation of AXL against therapy with an anticancer agent is non-small cell lung cancer or head-and-neck cancer, having activating mutations of EGFR which has acquired resistance to therapy with an EGFR inhibitor, and in one aspect, the pharmaceutical composition as described in (1-1) or (2-1); the use as described in (1-2) or (2-2); the use as described in (1-3) or (2-3); the compound A as described in (1-4) or hemifumarate of the compound A as described in (2-4); or the treating method as described in (1-5) or (2-5), in which the cancer which has acquired resistance by the activation of AXL against therapy with an anticancer agent is non-small cell lung cancer with activating mutations of EGFR, which has acquired resistance to therapy with an EGFR inhibitor.

(6-1) A pharmaceutical composition for treating AXL-related cancer, comprising the compound A or a pharmaceutically acceptable salt thereof, and a pharmaceutically acceptable excipient, in which the pharmaceutical composition is used in combination with an EGFR inhibitor, in one aspect, the pharmaceutical composition as described in (1-1), in which the pharmaceutical composition is used in combination with the EGFR inhibitor, in another aspect, the pharmaceutical composition as described in (2-1), in which the pharmaceutical composition is used in combination with the EGFR inhibitor, in a still another aspect, the pharmaceutical composition as described in (3), in which the pharmaceutical composition is used in combination with the EGFR inhibitor, in a still another aspect, the pharmaceutical composition as described in (4), in which the pharmaceutical composition is used in combination with the EGFR inhibitor, in a still another aspect, the pharmaceutical composition as described in (5), in which the pharmaceutical composition is used in combination with the EGFR inhibitor, in a still another aspect, the pharmaceutical composition for treating cancer which has acquired resistance by the activation of AXL against therapy with an anticancer agent as described in (1-1), in which the pharmaceutical composition is used in combination with the EGFR inhibitor, in a still another aspect, the pharmaceutical composition for treating cancer which has acquired resistance by the activation of AXL against therapy with an anticancer agent as described in (2-1), in which the pharmaceutical composition is used in combination with the EGFR inhibitor, in a still another aspect, the pharmaceutical composition for treating cancer which has acquired resistance by the activation of AXL against therapy with an anticancer agent as described in (3), in which the pharmaceutical composition is used in combination with the EGFR inhibitor, in a still another aspect, the pharmaceutical composition for treating cancer which has acquired resistance by the activation of AXL against therapy with an anticancer agent as described in (4), in which the pharmaceutical composition is used in combination with the EGFR inhibitor, and in a still another aspect, the pharmaceutical composition for treating cancer which has acquired resistance by the activation of AXL against therapy with an anticancer agent as described in (5), in which the pharmaceutical composition is used in combination with the EGFR inhibitor.

(6-2) Use of the compound A or a pharmaceutically acceptable salt thereof for the manufacture of a pharmaceutical composition for treating AXL-related cancer, in which the use is used in combination with an EGFR inhibitor, in one aspect, the use as described in (1-2), in which the use is used in combination with an EGFR inhibitor, in another aspect, the use as described in (2-2), in which the use is used in combination with an EGFR inhibitor, in a still another aspect, the use as described in (3), in which the use is used in combination with an EGFR inhibitor, in a still another aspect, the use as described in (4), in which the use is used in combination with an EGFR inhibitor, and in a still another aspect, the use as described in (5), in which the use is used in combination with the EGFR inhibitor. Furthermore, in a still another aspect, the use for the manufacture of a pharmaceutical composition for treating cancer which has acquired resistance by the activation of AXL against therapy with an anticancer agent as described in (1-2), in which the use is used in combination with an EGFR inhibitor, in a still another aspect, the use for the manufacture of a pharmaceutical composition for treating cancer which has acquired resistance by the activation of AXL against therapy with an anticancer agent as described in (2-2), in which the use is used in combination with an EGFR inhibitor, in a still another aspect, the use for the manufacture of a pharmaceutical composition for treating cancer which has acquired resistance by the activation of AXL against therapy with an anticancer agent as described in (3), in which the use is used in combination with an EGFR inhibitor, in a still another aspect, the use for the manufacture of a pharmaceutical composition for treating cancer which has acquired resistance by the activation of AXL against therapy with an anticancer agent as described in (4), in which the use is used in combination with an EGFR inhibitor, in a still another aspect, the use for the manufacture of a pharmaceutical composition for treating cancer which has acquired resistance by the activation of AXL against therapy with an anticancer agent as described in (5), in which the use is used in combination with the EGFR inhibitor.

(6-3) Use of the compound A or a pharmaceutically acceptable salt thereof for treating AXL-related cancer, in which the use is used in combination with an EGFR inhibitor, in one aspect, the use as described in (1-3), in which the use is used in combination with an EGFR inhibitor, in another aspect, the use as described in (2-3), in which the use is used in combination with an EGFR inhibitor, in a still another aspect, the use as described in (3), in which the use is used in combination with an EGFR inhibitor, in a still another aspect, the use as described in (4), in which the use is used in combination with an EGFR inhibitor, and in a still another aspect, the use as described in (5), in which the use is used in combination with the EGFR inhibitor. Furthermore, in a still another aspect, the use for treating cancer which has acquired resistance by the activation of AXL against therapy with an anticancer agent as described in (1-3), in which the use is used in combination with an EGFR inhibitor, in a still another aspect, the use for treating cancer which has acquired resistance by the activation of AXL against therapy with an anticancer agent as described in (2-3), in which the use is used in combination with an EGFR inhibitor, in a still another aspect, the use for treating cancer which has acquired resistance by the activation of AXL against therapy with an anticancer agent as described in (3), in which the use is used in combination with an EGFR inhibitor, in a still another aspect, the use for treating cancer which has acquired resistance by the activation of AXL against therapy with an anticancer agent as described in (4), in which the use is used in combination with an EGFR inhibitor, and in a still another aspect, the use for treating cancer which has acquired resistance by the activation of AXL against therapy with an anticancer agent as described in (5), in which the use is used in combination with the EGFR inhibitor.

(6-4) The compound A or a pharmaceutically acceptable salt thereof for treating AXL-related cancer, which is used in combination with an EGFR inhibitor, in one aspect, the compound A as described in (1-4) or hemifumarate of the compound A as described in (2-4), which is used in combination with an EGFR inhibitor, in another aspect, the compound A or hemifumarate of the compound A as described in (3), which is used in combination with an EGFR inhibitor, in a still another aspect, the compound A or hemifumarate of the compound A as described in (4), which is used in combination with an EGFR inhibitor, and in a still another aspect, the compound A or hemifumarate of the compound A as described in (5), which is used in combination with the EGFR inhibitor. Furthermore, in a still another aspect, the compound A for treating cancer which has acquired resistance by the activation of AXL against therapy with an anticancer agent as described in (1-4) or hemifumarate of the compound A for treating cancer which has acquired resistance by the activation of AXL against therapy with an anticancer agent as described in (2-4), which is used in combination with an EGFR inhibitor, in another aspect, the compound A or hemifumarate of the compound A for treating cancer which has acquired resistance by the activation of AXL against therapy with an anticancer agent as described in (3), which is used in combination with an EGFR inhibitor, in a still another aspect, the compound A or hemifumarate of the compound A for treating cancer which has acquired resistance by the activation of AXL against therapy with an anticancer agent as described in (4), which is used in combination with an EGFR inhibitor; and the compound A or hemifumarate of the compound A for treating cancer which has acquired resistance by the activation of AXL against therapy with an anticancer agent as described in (5), which is used in combination with the EGFR inhibitor.

(6-5) A method for treating AXL-related cancer, comprising administering an effective amount of the compound A or a pharmaceutically acceptable salt thereof to a subject, in which the method is used in combination with an EGFR inhibitor, in one aspect, the treating method as described in (1-5), in which the method is used in combination with an EGFR inhibitor, in another aspect, the treating method as described in (2-5), in which the method is used in combination with an EGFR inhibitor; in a still another aspect, the treating method as described in (3), in which the method is used in combination with an EGFR inhibitor, in a still another aspect, the treating method as described in (4), in which the method is used in combination with an EGFR inhibitor, and in a still another aspect, the treating method as described in (5), in which the method is used in combination with the EGFR inhibitor. Furthermore, in a still another aspect, the method for treating cancer which has acquired resistance by the activation of AXL against therapy with an anticancer agent as described in (1-5), in which the method is used in combination with an EGFR inhibitor, in still another aspect, the method for treating cancer which has acquired resistance by the activation of AXL against therapy with an anticancer agent as described in (2-5), in which the method is used in combination with an EGFR inhibitor, in a still another aspect, the method for treating cancer which has acquired resistance by the activation of AXL against therapy with an anticancer agent as described in (3), in which the method is used in combination with an EGFR inhibitor, in a still another aspect, the method for treating cancer which has acquired resistance by the activation of AXL against therapy with an anticancer agent as described in (4), in which the method is used in combination with an EGFR inhibitor, and in a still another aspect, the method for treating cancer which has acquired resistance by the activation of AXL against therapy with an anticancer agent as described in (5), in which the method is used in combination with the EGFR inhibitor.

(7-1) The pharmaceutical composition as described in (6-1), in which the EGFR inhibitor used in combination is erlotinib, gefitinib, or lapatinib, in one aspect, the pharmaceutical composition as described in (6-1), in which the EGFR inhibitor used in combination is erlotinib or gefitinib, and in another aspect, the pharmaceutical composition as described in (6-1), in which the EGFR inhibitor used in combination is erlotinib.

(7-2) The use as described in (6-2), in which the EGFR inhibitor used in combination is erlotinib, gefitinib, or lapatinib, in one aspect, the use as described in (6-2), in which the EGFR inhibitor used in combination is erlotinib or gefitinib, and in another aspect, the use as described in (6-2), in which the EGFR inhibitor used in combination is erlotinib.

(7-3) The use as described in (6-3), in which the EGFR inhibitor used in combination is erlotinib, gefitinib, or lapatinib, in one aspect, the use as described in (6-3), in which the EGFR inhibitor used in combination is erdotinib or gefitinib, and in another aspect, the use as described in (6-3), in which the EGFR inhibitor used in combination is erlotinib.

(7-4) The compound A or hemifumarate of the compound A as described in (6-4), in which the EGFR inhibitor used in combination is erdotinib, gefitinib, or lapatinib, in one aspect, the compound A or hemifumarate of the compound A as described in (6-4), in which the EGFR inhibitor used in combination is erdotinib or gefitinib, and in another aspect, the compound A or hemifumarate of the compound A as described in (6-4), in which the EGFR inhibitor used in combination is erdotinib.

(7-5) The treating method as described in (6-5), in which the EGFR inhibitor used in combination is erdotinib, gefitinib, or lapatinib, in one aspect, the treating method as described in (6-5), in which the EGFR inhibitor used in combination is erlotinib or gefitinib, and in another aspect, the treating method as described in (6-5), in which the EGFR inhibitor used in combination is erlotinib.

(8-1) A pharmaceutical composition for treating cancer which has acquired resistance by the activation of AXL against therapy with an anticancer agent, comprising the compound A or a pharmaceutically acceptable salt thereof, and a pharmaceutically acceptable excipient, in which the pharmaceutical composition is used in combination with an anticancer agent.

(8-2) A pharmaceutical composition for treating non-small cell lung cancer, head-and-neck cancer, or triple negative breast cancer having activating mutations of EGFR which has acquired resistance to therapy with an EGFR inhibitor, comprising the compound A or a pharmaceutically acceptable salt thereof, and a pharmaceutically acceptable excipient, in which the pharmaceutical composition is used in combination with the EGFR inhibitor.

(8-3) A pharmaceutical composition for treating acute myeloid leukemia or astrocytoma which has acquired resistance to chemotherapy, comprising the compound A or a pharmaceutically acceptable salt thereof, and a pharmaceutically acceptable excipient, in which the pharmaceutical composition is used in combination with a chemotherapeutic agent.

(8-4) A pharmaceutical composition for treating non-EGFR mutation-positive lung cancer which has acquired resistance to therapy with cisplatin, comprising the compound A or a pharmaceutically acceptable salt thereof, and a pharmaceutically acceptable excipient, in which the pharmaceutical composition is used in combination with cisplatin.

(9-1) Use of the compound A or a pharmaceutically acceptable salt thereof for the manufacture of a pharmaceutical composition for treating cancer which has acquired resistance by the activation of AXL against therapy with an anticancer agent, in which the use is used in combination with the anticancer agent.

(9-2) Use of the compound A or a pharmaceutically acceptable salt thereof for the manufacture of a pharmaceutical composition for treating non-small cell lung cancer, head-and-neck cancer, or triple negative breast cancer having activating mutations of EGFR which has acquired resistance to therapy with an EGFR inhibitor, in which the use is used in combination with the EGFR inhibitor.

(9-3) Use of the compound A or a pharmaceutically acceptable salt thereof for the manufacture of a pharmaceutical composition for treating acute myeloid leukemia or astrocytoma which has acquired resistance to chemotherapy, in which the use is used in combination with a chemotherapeutic agent.

(9-4) Use of the compound A or a pharmaceutically acceptable salt thereof for the manufacture of a pharmaceutical composition for treating non-EGFR mutation-positive lung cancer which has acquired resistance to therapy with cisplatin, in which the use is used in combination with cisplatin.

(10-1) Use of the compound A or a pharmaceutically acceptable salt thereof for treating cancer which has acquired resistance by the activation of AXL against therapy with an anticancer agent, in which the use is used in combination with the anticancer agent.

(10-2) Use of the compound A or a pharmaceutically acceptable salt thereof for treating non-small cell lung cancer, head-and-neck cancer, or triple negative breast cancer having activating mutations of EGFR which has acquired resistance to therapy with an EGFR inhibitor, in which the use is used in combination with the EGFR inhibitor.

(10-3) Use of the compound A or a pharmaceutically acceptable salt thereof for treating acute myeloid leukemia or astrocytoma which has acquired resistance to chemotherapy, in which the use is used in combination with a chemotherapeutic agent.

(10-4) Use of the compound A or a pharmaceutically acceptable salt thereof for treating non-EGFR mutation-positive lung cancer which has acquired resistance to therapy with cisplatin, in which the use is used in combination with cisplatin.

(11-1) The compound A or a pharmaceutically acceptable salt thereof for treating cancer which has acquired resistance by the activation of AXL against therapy with an anticancer agent, in which the compound A or a pharmaceutically acceptable salt thereof is used in combination with the anticancer agent.

(11-2) The compound A or a pharmaceutically acceptable salt thereof for treating non-small cell lung cancer, head-and-neck cancer, or triple negative breast cancer having activating mutations of EGFR which has acquired resistance to therapy with an EGFR inhibitor, in which the compound A or a pharmaceutically acceptable salt thereof is used in combination with the EGFR inhibitor.

(11-3) The compound A or a pharmaceutically acceptable salt thereof for treating acute myeloid leukemia or astrocytoma which has acquired resistance to chemotherapy, in which the compound A or a pharmaceutically acceptable salt thereof is used in combination with a chemotherapeutic agent.

(11-4) The compound A or a pharmaceutically acceptable salt thereof for treating non-EGFR mutation-positive lung cancer which has acquired resistance to therapy with cisplatin, in which the compound A or a pharmaceutically acceptable salt thereof is used in combination with cisplatin.

(12-1) A method for treating cancer which has acquired resistance by the activation of AXL against therapy with an anticancer agent, comprising administering an effective amount of the compound A or a pharmaceutically acceptable salt thereof to a subject, in which the method is used in combination with the anticancer agent.

(12-2) A method for treating non-small cell lung cancer, head-and-neck cancer, or triple negative breast cancer having activating mutations of EGFR which has acquired resistance to therapy with an EGFR inhibitor, comprising administering an effective amount of the compound A or a pharmaceutically acceptable salt thereof to a subject, in which the method is used in combination with the EGFR inhibitor.

(12-3) A method for treating acute myeloid leukemia or astrocytoma which has acquired resistance to chemotherapy, comprising administering an effective amount of the compound A or a pharmaceutically acceptable salt thereof to a subject, in which the method is used in combination with the chemotherapeutic agent.

(12-4) A method for treating non-EGFR mutation-positive lung cancer which has acquired resistance to therapy with cisplatin, comprising administering an effective amount of the compound A or a pharmaceutically acceptable salt thereof to a subject, in which the method is used in combination with cisplatin.

(13-1) An agent for treating cancer which has acquired resistance by the activation of AXL against therapy with an anticancer agent, comprising the compound A or a pharmaceutically acceptable salt thereof, in which the agent is used in combination with an anticancer agent.

(13-2) An agent for treating non-small cell lung cancer, head-and-neck cancer, or triple negative breast cancer having activating mutations of EGFR which has acquired resistance to therapy with an EGFR inhibitor, comprising the compound A or a pharmaceutically acceptable salt thereof, in which the agent is used in combination with the EGFR inhibitor.

(13-3) An agent for treating acute myeloid leukemia or astrocytoma which has acquired resistance to chemotherapy, comprising the compound A or a pharmaceutically acceptable salt thereof, in which the agent is used in combination with a chemotherapeutic agent.

(13-4) An agent for treating non-EGFR mutation-positive lung cancer which has acquired resistance to therapy with cisplatin, comprising the compound A or a pharmaceutically acceptable salt thereof, in which the agent is used in combination with cisplatin.

(14-1) A pharmaceutical composition for treating EGFR mutation-positive non-small cell lung cancer, comprising the compound A or a pharmaceutically acceptable salt thereof, and a pharmaceutically acceptable excipient, in which the pharmaceutical composition is used in combination with the EGFR inhibitor.

(14-2) Use of the compound A or a pharmaceutically acceptable salt thereof for the manufacture of a pharmaceutical composition for treating EGFR mutation-positive non-small cell lung cancer, in which the use is used in combination with an EGFR inhibitor.

(14-3) Use of the compound A or a pharmaceutically acceptable salt thereof for treating EGFR mutation-positive non-small cell lung cancer, in which the use is used in combination with an EGFR inhibitor.

(14-4) The compound A or a pharmaceutically acceptable salt thereof used for treating EGFR mutation-positive non-small cell lung cancer, in which the compound A or a pharmaceutically acceptable salt thereof is used in combination with an EGFR inhibitor.

(14-5) A method for treating EGFR mutation-positive non-small cell lung cancer, comprising administering an effective amount of the compound A or a pharmaceutically acceptable salt thereof to a subject, in which the method is used in combination with an EGFR inhibitor.

(14-6) An agent for treating EGFR mutation-positive non-small cell lung cancer, comprising the compound A or a pharmaceutically acceptable salt thereof, in which the agent is used in combination with an EGFR inhibitor.

(15-1) A pharmaceutical composition for treating AXL-related cancer, comprising the compound A or a pharmaceutically acceptable salt thereof, and a pharmaceutically acceptable excipient.

(15-2) The pharmaceutical composition as described in (15-1), in which the AXL-related cancer is cancer with high expression of AXL.

(15-3) The pharmaceutical composition as described in (15-1), in which the AXL-related cancer is cancer which has acquired resistance by the activation of AXL against therapy with an anticancer agent.

(15-4) The pharmaceutical composition as described in (15-3), in which the cancer which has acquired resistance by the activation of AXL against therapy with an anticancer agent is non-small cell lung cancer with activating mutations of EGFR, which has acquired resistance to therapy with an EGFR tyrosine kinase inhibitor.

(15-5) The pharmaceutical composition as described in (15-4), which is used in combination with the EGFR tyrosine kinase inhibitor.

(15-6) The pharmaceutical composition as described in (15-5), in which the EGFR tyrosine kinase inhibitor is an EGFR tyrosine kinase inhibitor selected from the group consisting of erlotinib, gefitinib, and lapatinib.

(15-7) The pharmaceutical composition as described in (15-6), in which the EGFR tyrosine kinase inhibitor is erlotinib.

(15-8) The pharmaceutical composition as described in any one of (15-1) to (15-7), in which the compound A or a pharmaceutically acceptable salt thereof is the compound A.

(15-9) The pharmaceutical composition as described in any one of (15-1) to (15-7), in which the compound A or a pharmaceutically acceptable salt thereof is hemifumarate of the compound A.

(16-1) A pharmaceutical composition for treating AXL-related cancer, comprising the compound A or a pharmaceutically acceptable salt thereof, an EGFR tyrosine kinase inhibitor, and a pharmaceutically acceptable excipient.

(16-2) The pharmaceutical composition as described in (16-1), in which the AXL-related cancer is cancer with high expression of AXL.

(16-3) The pharmaceutical composition as described in (16-1), in which the AXL-related cancer is cancer which has acquired resistance by the activation of AXL against therapy with an anticancer agent.

(16-4) The pharmaceutical composition as described in (16-3), in which the cancer which has acquired resistance by the activation of AXL against therapy with an anticancer agent is non-small cell lung cancer with activating mutations of EGFR, which has acquired resistance to therapy with an EGFR tyrosine kinase inhibitor.

(16-5) The pharmaceutical composition as described in (16-4), in which the EGFR tyrosine kinase inhibitor is an EGFR tyrosine kinase inhibitor selected from the group consisting of erlotinib, gefitinib, and lapatinib.

(16-6) The pharmaceutical composition as described in (16-5), in which the EGFR tyrosine kinase inhibitor is erlotinib.

(16-7) The pharmaceutical composition as described in (16-6), in which the pharmaceutical composition is an oral administration agent.

(16-8) The pharmaceutical composition as described in (16-6), in which the pharmaceutical composition is an injectable liquid preparation.

The compound A or a pharmaceutically acceptable salt thereof is available by the method described in Patent Document 1 (Pamphlet of International Publication No. 2010/128659) or a modified method thereof.

Furthermore, "the pharmaceutically acceptable salt of the compound A" means an acid addition salt of the compound A, and specific examples thereof include acid addition salts with inorganic acids such as hydrochloric acid, hydrobromic acid, hydroiodic acid, sulfuric acid, nitric acid, and phosphoric acid, or with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, and glutamic acid. In addition, "the pharmaceutically acceptable salt of the compound A" encompasses solvates, specifically hydrates and ethanolates of the compound A, as well as acid addition salts of the solvates of the compound A.

In addition, in one aspect, examples of the "compound A or a pharmaceutically acceptable salt thereof" include the compound A, in another aspect, an acid addition salt of the compound A with fumaric acid, and in a still another aspect, hemifumarate of the compound A.

Pharmaceutical compositions comprising the compound A or a pharmaceutically acceptable salt thereof can be prepared using excipients which are usually used in the art, that is, excipients for pharmaceutical preparation, carriers for pharmaceutical preparation, and the like in accordance with the methods which are usually used.

Administration can be accomplished either by oral administration via tablets, pills, capsules, granules, powders, solutions, and the like, or parenteral administration, such as injections such as intraarticular, intravenous, and intramuscular injections, suppositories, transdermal solutions, ointments, transdermal patches, transmucosal solutions, transmucosal patches, inhalers, and the like.

Solid compositions for oral administration are used in the form of tablets, powders, granules, or the like. In such solid compositions, one or more active ingredients are mixed with at least one inactive excipient. In a conventional method, the composition may contain inactive additives, such as lubricants, disintegrating agents, stabilizers, or solubilization assisting agents. If necessary, tablets or pills may be coated with sugar or gastric- or enteric-soluble substance films.

Liquid compositions for oral administration include pharmaceutically acceptable emulsions, solutions, suspensions, syrups, elixirs, or the like, and also include generally used inert diluents, for example, purified water or ethanol. In addition to the inert diluent, liquid compositions may also contain auxiliary agents, such as solubilization assisting agents, moistening agents, and suspending agents, sweeteners, flavors, aromatics, or antiseptics.

Injections for parenteral administration include sterile aqueous or non-aqueous solutions, suspensions, or emulsions. Aqueous solvents include, for example, distilled water for injection or physiological saline. Examples of non-aqueous solvents include alcohols such as ethanol. Such compositions may further contain tonicity agents, antiseptics, moistening agents, emulsifying agents, dispersing agents, stabilizers, or solubilization assisting agents. These are sterilized, for example, by filtration through bacteria retaining filter, blendings of bactericide, or irradiation. In addition, these can also be used by preparing sterile solid compositions, and dissolving or suspending in sterile water or sterile solvents for injection prior to use.

In general, for oral administration, the daily dose is about 0.001 mg/kg to 100 mg/kg, preferably 0.01 mg/kg to 30 mg/kg, and more preferably 0.1 to 10 mg/kg, per body weight, administered in one portion or in 2 to 4 separate portions. In the case of intravenous administration, the daily dose is suitably administered from about 0.0001 mg/kg to 10 mg/kg per body weight, once a day or two or more times a day. In addition, a transmucosal agent is administered at a dose from about 0.001 mg/kg to 100 mg/kg per body weight, once a day or two or more times a day. Doses are determined as appropriate according to the individual according to the symptoms, age, gender, and the like.

Although varying depending on administration routes, formulations, administration sites, or the types of excipients or additives, the pharmaceutical composition of the present invention contains 0.01% by weight to 99% by weight, and in one aspect, 0.01% by weight to 50% by weight of the compound A or a pharmaceutically acceptable salt thereof as an active ingredient.

The pharmaceutical composition of the present invention can be used in combination with various therapeutic agents that are considered effective for cancer, in particular, AXL-related cancer. The combined preparations may be administered simultaneously, or separately and continuously, or at a desired time interval. The preparations to be administered simultaneously may be a mixture, or may be prepared individually. In particular, examples of the agents that can be used in combination herein include EGFR tyrosine kinase inhibitors such as erlotinib, gefitinib, and lapatinib, HER2 kinase inhibitors such as trastuzumab, and platinum agents such as cisplatin and carboplatin.

EXAMPLES

The pharmacological effects of the pharmaceutical composition of the present invention were confirmed by Examples below.

Example 1 Evaluation of AXL Kinase Inhibitory Activity of Compound A

The compound A was dissolved in dimethyl sulfoxide (DMSO) to prepare a solution at a 100-fold concentration as compared to the test concentration. The solution was 25-fold diluted with an assay buffer (20 mM HEPES, 0.01% Triton X-100, 2 mM DTT, pH 7.5) to obtain a test material solution. As an enzyme to be used for the reaction, one obtained by expressing a region including a kinase domain in a baculovirus, followed by purification.

5 μL of the test material solution at a 4-fold concentration, prepared using an assay buffer (20 mM HEPES, 0.01% Triton X-100, 2 mM DTT, pH 7.5), 5 μL of a substrate/ATP/metal solution at a 4-fold concentration, and 10 μL of a kinase solution at a 2-fold concentration were mixed within a well in a polypropylene-made 384-well plate, and left to undergo a reaction at room temperature for 1 hour. The substrate was used with CSKtide at a final concentration of 1000 nM, ATP at a final concentration of 50 M, and Mg at a final concentration of 5 mM. Thereafter, 60 μL of a termination buffer (QuickScout Screening Assist MSA (Carna Biosciences)) was added thereto to stop the reaction.

The substrate peptide and the phosphorylated peptide in the reaction solution were separated using a LabChip3000 system (Caliper Life Science), and quantitated. The kinase reaction was evaluated using a product ratio (P/(P+S)) calculated from the substrate peptide peak height (S) and the phosphorylated peptide peak height (P).

For the data analysis, by defining the average signal of a control well including all the reaction components as 0% inhibition and defining the average signal of a background well including all the reaction components except for the enzyme as 100% inhibition, the inhibition rate was calculated from the average signal of the wells for testing the respective test materials. The $IC_{50}$ value was determined by approximating the plots from the test material concentrations and the inhibition rates to a logistic curve with 4 parameters by a nonlinear least-squares method.

As a result, the compound A inhibited the AXL kinase activity at a concentration of 0.70 nM as the $IC_{50}$ value.

Example 2 Evaluation of Proliferation Inhibition (In Vitro) Using AXL Forced Expression Cells Established from Human Non-Small Cell Lung Cancer Cell Line PC9 Cells (Activating Mutation Type EGFR Expression Cells)

4 μg of a pMXs vector (named AXL/pMXs) including a full-length AXL ORF (Gene Bank accession no.: NM_001699) was introduced into GP2-293 packaging cells (Life Technologies), using a transfection reagent (LipofectAmine 2000 (Life Technologies)) together with 1 μg of a packaging plasmid VSV-G (Takara Bio Company). The culture supernatant after two days from the introduction was recovered as a retrovirus, and Polybrene (Sigma) was added thereto to a final concentration of 6 μg/mL, followed by addition to a human non-small cell lung cancer cell line PC9 cells. After 2 days, the culture supernatant of the PC9 cells were replaced by one obtained by adding a 10% bovine serum (Invitrogen) and Puromycin (Invitrogen) to an RPMI 1640 Medium (Sigma) to a final concentration of 0.1 μg/mL, and continuously cultured for one week to perform agent selection. As a control cell, a cell to which pMXs had been introduced by the same procedure was prepared and named PC9 vec. Further, for the AXL/pMXs-introduced cell, erlotinib at a final concentration of 300 nM was added to the medium and treated for 3 days to concentrate highly AXL-expressed cells, thereby obtaining PC9 cells stably expressing AXL (named PC9/AXL).

The obtained PC9/AXL cells and PC9 vec. cells were inoculated into a 384-well plate, respectively, using an RPMI 1640 medium (Sigma). On the same day, a DMSO solution of the test compound depending on the test concentration or DMSO alone was added thereto, followed by culturing at 37° C. for 4 days in the presence of 5% $CO_2$. Thereafter, the number of cells was measured using a cell count reagent (CellTiter-Glo™ Luminescent Cell Viability Assay (Promega)). By defining the measured value for the DMSO group as 0% inhibition and defining the measured value for the well having only the medium in which the cells had not been inoculated as 100% inhibition, the inhibition rate of the test compound was calculated. As the test compound, a 100 nM compound A and erlotinib were used.

As a result, erlotinib inhibited the proliferation of the PC9 vec. cells and its $IC_{50}$ value was 108 nM. Further, for the AXL/PC9 cells, erlotinib did not inhibit the proliferation by 50% or more, and the survival rate of the cells even at a maximum concentration of 3000 nM was 73%. On the other hand, for the proliferation-inhibiting action by combined use of the compound A and erlotinib, the proliferation of the AXL/PC9 cells were inhibited by 50% or more, and erlotinib in the presence of the compound A at 100 nM inhibited the proliferation of the AXL/PC9 cell lines at an $IC_{50}$ value of 56 nM.

Here, the phosphorylated AXL in the AXL/PC9 cells was confirmed by Western blot using a phospho-AXL antibody (R&D Inc.), and thus, it was considered that AXL phosphorylation was completely inhibited in the presence of the compound A at 100 nM, and thus, the AXL activity was inhibited.

From the above, it was confirmed that the compound A released the resistance to erlotinib through inhibition of AXL activation, and thus exhibited a cell proliferation inhibiting action in the AXL/PC9 cell lines.

Example 3 Anti-Tumor Evaluation (In Vivo) by Combined Use of Compound A and Erlotinib for Erlotinib-Resistant HCC827 Subcutaneous Cancer-Bearing Mouse Model HCC827 cells (EGFR mutation-positive lung cancer cell line) were subcutaneously implanted to a dorsal part of an immunodeficient mouse (CB17/Icr-Prkdcscid/CrlCrlj, male, 4-week-old (Charles River Laboratories Japan, Inc.)) to prepare HCC827 subcutaneous cancer-bearing mice. After tumor engraftment, erlotinib was orally administered at a dose of 12.5 mg/kg/day once per day for 40 days to construct an erlotinib-resistant HCC827 subcutaneous cancer-bearing mouse model. Further, the HCC827 cell line is erlotinib-sensitive, but is known to acquire resistance to erlotinib by erlotinib exposure, and exhibit overexpression of AXL. In addition, it is known that when AXL is suppressed in molecular biology techniques in this cell, the sensitivity to erlotinib is restored and a stable cell line expressing AXL of an AXL gene-introduced HCC827 exhibits erlotinib resistance (Nat. Genet. 2012 Jul. 1; 44(8): 852-60).

To the erlotinib-resistant HCC827 subcutaneous cancer-bearing mouse model was administered erlotinib (erlotinib alone-administered group: 12.5 mg/kg/day, QD, po (n=8)), the compound A (the compound A alone-administered group: 30 mg/kg/day, QD, po (n=8)), or erlotinib (12.5 mg/kg/day) and the compound A (30 mg/kg/day) (group with combined use of erlotinib and the compound A, QD, po (n=7)), and the change in the tumor volume was measured over time. The tumor volume measured on the day before the starting day of administration to the constructed erlotinib-resistant HCC827 subcutaneous cancer-bearing mouse model was used as a value on the starting day of administration to the constructed erlotinib-resistant HCC827 subcutaneous cancer-bearing mouse model.

The results are shown in FIG. 1.

Upon comparison of the tumor volume on the starting day of administration to the constructed erlotinib-resistant HCC827 subcutaneous cancer-bearing mouse model with that after 12 days, the erlotinib alone-administered group showed an increase in the tumor volume from 335.8 $mm^3$ to 484.1 $mm^3$, and the compound A alone-administered group showed an increase in the tumor volume from 339.2 $mm^3$ to 739.2 $mm^3$. On the other hand, the group with combined use of erlotinib and the compound A showed a decrease in the tumor volume from 341.9 $mm^3$ to 184.7 $mm^3$.

These results demonstrated that for cancer which has acquired resistance to administration of erlotinib which is an EGFR inhibitor, the erlotinib alone-administered group or the compound A alone-administered group did not show a tumor decreasing effect, while the group with combined use of erlotinib and the compound A exhibited the tumor decreasing effect.

From the above, it was confirmed that in the erlotinib-resistant HCC827 subcutaneous cancer-bearing mouse model, the compound A induced decrease in the tumor volume by use of erlotinib in combination therewith.

Example 4 Anti-Tumor Evaluation (In Vivo) by Combined Use of Compound A and Erlotinib for Anticancer Agent-Untreated, HCC827 Subcutaneous Cancer-Bearing Mouse In the same manner as in Example 3, an HCC827 subcutaneous cancer-bearing mice were prepared. After tumor engraftment, to the HCC827 subcutaneous cancer-bearing mouse were administered a vehicle, erlotinib (erlotinib alone-administered group: 12.5 mg/kg/day, QD, po (n=5)), the compound A (the compound A alone-administered group: 30 mg/kg/day, QD, po (n=5)), or both of erlotinib (12.5 mg/kg/day) and the compound A (10 mg/kg/day or 30 mg/kg/day) (group with combined use of erlotinib and the compound A: QD, po (n=5)), and the change in the tumor volume was measured over time.

Figure 2:
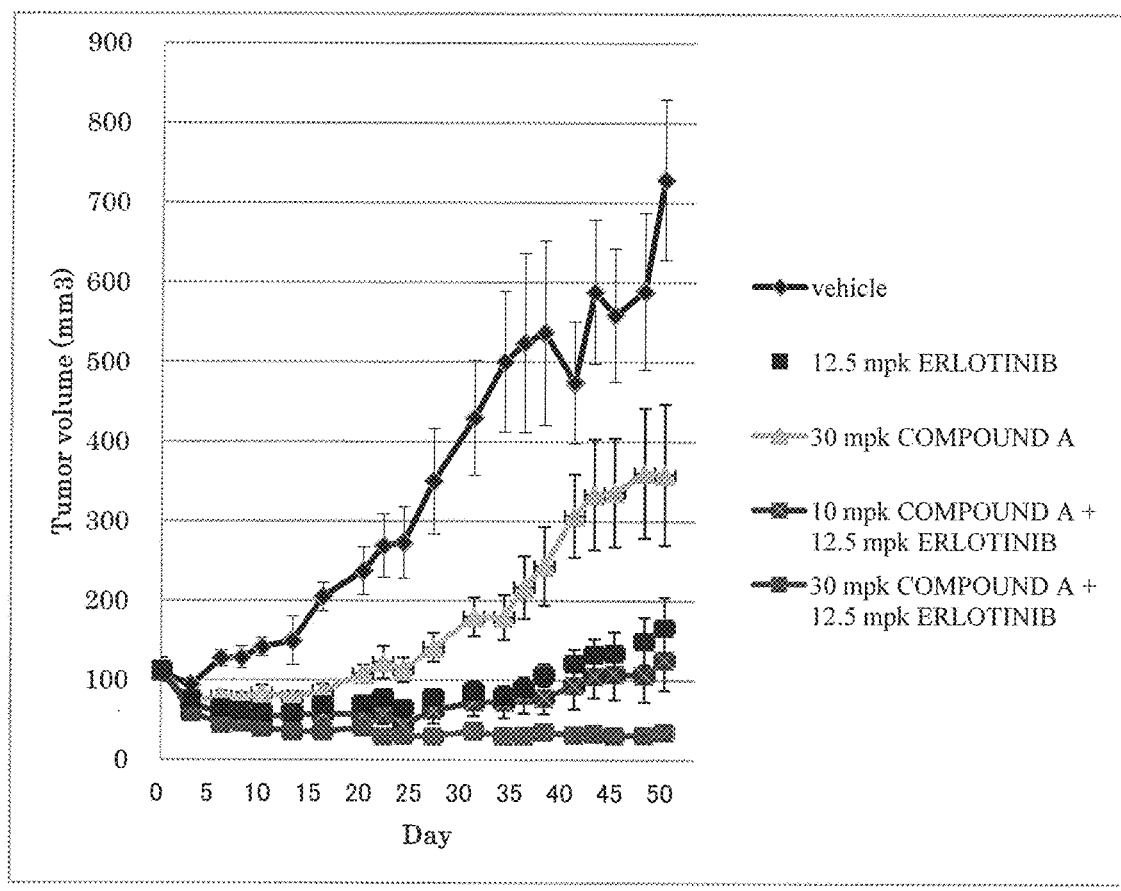
FIG. 2 is a view showing the tumor volumes of the model animals in the erlotinib-administered group, the compound A-administered group, and the group with combined use of erlotinib and the compound A, for the HCC827 subcutaneous cancer-bearing mouse (not treated with an anticancer agent). The vertical axis indicates the tumor volumes and the horizontal axis indicates the number of days.

The results are shown in FIG. 2.

The erdotinib alone-administered group first showed decrease in the tumor volume, but starting from about one month after the initiation of administration, the reproliferation of tumor was observed. On the other hand, the group with combined use of erotinib and the compound A exhibited a strong tumor regression action in the compound A dose-dependent manner, as compared with the erlotinib alone-administered group, and further, in the group with combined use of erlotinib and the compound A at 30 mg/kg/day, the reproliferation of tumor was not observed even one month after the administration.

From the above, it was confirmed that in the HCC827 subcutaneous cancer-bearing mouse model which is an EGFR mutation-positive lung cancer cell line, the compound A exhibited an enhanced and sustained tumor regression action by using erlotinib in combination therewith, as compared with effects of the erdotinib alone-administered group.

According to Examples 3 and 4 above, the anti-tumor action in the combined administration of erlotinib and the compound A can be evaluated, and in the HCC827 subcutaneous cancer-bearing mouse model which is an EGFR mutation-positive lung cancer cell line, an enhanced and sustained tumor regression action was confirmed by the combined use of erlotinib and the compound A, as compared with the effects of the erlotinib alone-administered group. That is, the compound A can be used, for example, as an active ingredient of a pharmaceutical composition for treating cancer in which the expression of AXL has increased by treatment with an EGFR inhibitor and, as a result, resistance to the EGFR inhibitor has been acquired.

By the above tests, it was confirmed that the compound A or a pharmaceutically acceptable salt thereof has an AXL inhibitory action. Further, the compound A or a pharmaceutically acceptable salt thereof inhibited the proliferation of cancer cells with high expression of AXL. In addition, it was confirmed that in the animal models bearing cancer cells with high expression of AXL, the use of erlotinib in combination therewith inhibited the proliferation of cancer. That is, it was confirmed that the proliferation of cancer with high expression of AXL due to the increased expression of AXL by the administration of an EGFR inhibitor was inhibited by using the compound A or a pharmaceutically acceptable salt thereof in combination with the EGFR inhibitor.

From the above, the compound A or a pharmaceutically acceptable salt thereof can be used as an active ingredient of a pharmaceutical composition for treating AXL-related cancer, cancer with high expression of AXL, or cancer which has acquired resistance by the activation of AXL against therapy with an anticancer agent. In particular, the compound A or a pharmaceutically acceptable salt thereof can be used for treating cancer which has acquired resistance by the activation of AXL against therapy with an anticancer agent, in combination with the anticancer agent.

INDUSTRIAL APPLICABILITY

The compound A or a pharmaceutically acceptable salt thereof which is an active ingredient of the pharmaceutical composition of the present invention has an AXL inhibitory action, and can be used as an active ingredient of a pharmaceutical composition for treating AXL-related cancer, in another aspect, a pharmaceutical composition for treating cancer with high expression of AXL, and in still another aspect, a pharmaceutical composition for treating cancer which has acquired resistance by the activation of AXL against therapy with an anticancer agent.

The invention claimed is:

1. A method of treating an AXL-related cancer, the method comprising:
   administering an effective amount of a pharmaceutical composition to a subject in need thereof,
   wherein the pharmaceutical composition comprises 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof, and a pharmaceutically acceptable excipient,
   wherein the AXL-related cancer is cancer which has acquired resistance by the activation of AXL against therapy with an anticancer agent, and
   wherein the cancer which has acquired resistance by the activation of AXL against therapy with an anticancer agent is acute myeloid leukemia, which has acquired resistance to chemotherapy.

2. The method of claim 1, wherein the AXL-related cancer is cancer with high expression of AXL.

3. The method of claim 1, further comprising administering an EGFR tyrosine kinase inhibitor to the subject.

4. The method of claim 3, wherein the EGFR tyrosine kinase inhibitor is at least one EGFR tyrosine kinase inhibitor selected from the group consisting of erlotinib, gefitinib, and lapatinib.

5. The method of claim 4, wherein the EGFR tyrosine kinase inhibitor is erlotinib.

6. The method of claim 1, wherein the 6-ethyl-3-({3-methoxy-4-[4-(4-methyl piperazin-1-yl)piperidin-1-yl]phenyl}amino)-5-(tetrahydro-2H-pyran-4-ylamino)pyrazine-2-carboxamide or a pharmaceutically acceptable salt thereof is 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide.

7. The method of claim 1, wherein the 6-ethyl-3-({3-methoxy-4-[4-(4-methyl piperazin-1-yl)piperidin-1-yl]phenyl}amino)-5-(tetrahydro-2H-pyran-4-ylamino)pyrazine-2-carboxamide or a pharmaceutically acceptable salt thereof is 6-ethyl-3-({3-methoxy-4-[4-(4-methylpiperazin- 1-yl)piperidin-1-yl]phenyl}amino)-5-(tetrahydro-2H-pyran-4-ylamino)pyrazine-2-carboxamide hemifumarate.

* * * * *